United States Patent
Huber et al.

(10) Patent No.: US 7,222,625 B2
(45) Date of Patent: May 29, 2007

(54) PRESSURE ULCER PROSTHESIS AND METHOD FOR TREATING AND/OR PREVENTING PRESSURE ULCERS

(75) Inventors: David E. Huber, Austinmer (AU); Craig R. Andrews, Mosman (AU)

(73) Assignee: Viater Medical Pty Limited, New South Wales (AU)

( * ) Notice: Subject to any disclaimer, the term of this patent is extended or adjusted under 35 U.S.C. 154(b) by 0 days.

(21) Appl. No.: 11/031,675

(22) Filed: Jan. 7, 2005

(65) Prior Publication Data
US 2006/0150983 A1    Jul. 13, 2006

(51) Int. Cl.
*A61F 13/00* (2006.01)
(52) U.S. Cl. ...................................... 128/889
(58) Field of Classification Search .............. 129/188, 129/889; 602/23, 26, 27, 62, 25, 61, 20, 602/21, 22, 60
See application file for complete search history.

(56) References Cited

U.S. PATENT DOCUMENTS

| 143,537 | A | * | 10/1873 | Silberschmidt ............. 602/27 |
| 364,942 | A | * | 6/1887 | Lee ............................... 602/6 |
| 4,349,016 | A | * | 9/1982 | Glassman et al. ........... 602/23 |
| 4,390,015 | A | * | 6/1983 | Clements ..................... 602/23 |
| 4,497,070 | A | * | 2/1985 | Cho .............................. 2/22 |
| 4,798,199 | A | * | 1/1989 | Hubbard et al. ............. 602/21 |
| 5,358,471 | A | * | 10/1994 | Klotz .......................... 602/21 |
| 5,415,623 | A | * | 5/1995 | Cherubini .................... 602/7 |

FOREIGN PATENT DOCUMENTS

AU    2003 204858    1/2004

* cited by examiner

*Primary Examiner*—Patricia Bianco
*Assistant Examiner*—Camtu Nguyen
(74) *Attorney, Agent, or Firm*—Ladas and Parry LLP

(57) ABSTRACT

A pressure ulcer prosthesis (10) having an elongated body (11) to support a patient's limb. The body (11) has a longitudinally extending support surface (13) that is arcuate and concave in transverse cross section. A distal end (12) having a surface (18) extends away from the surface (13) so as to diverge therefrom so that a portion of the limb adjacently surface (18) is released from pressure.

29 Claims, 4 Drawing Sheets

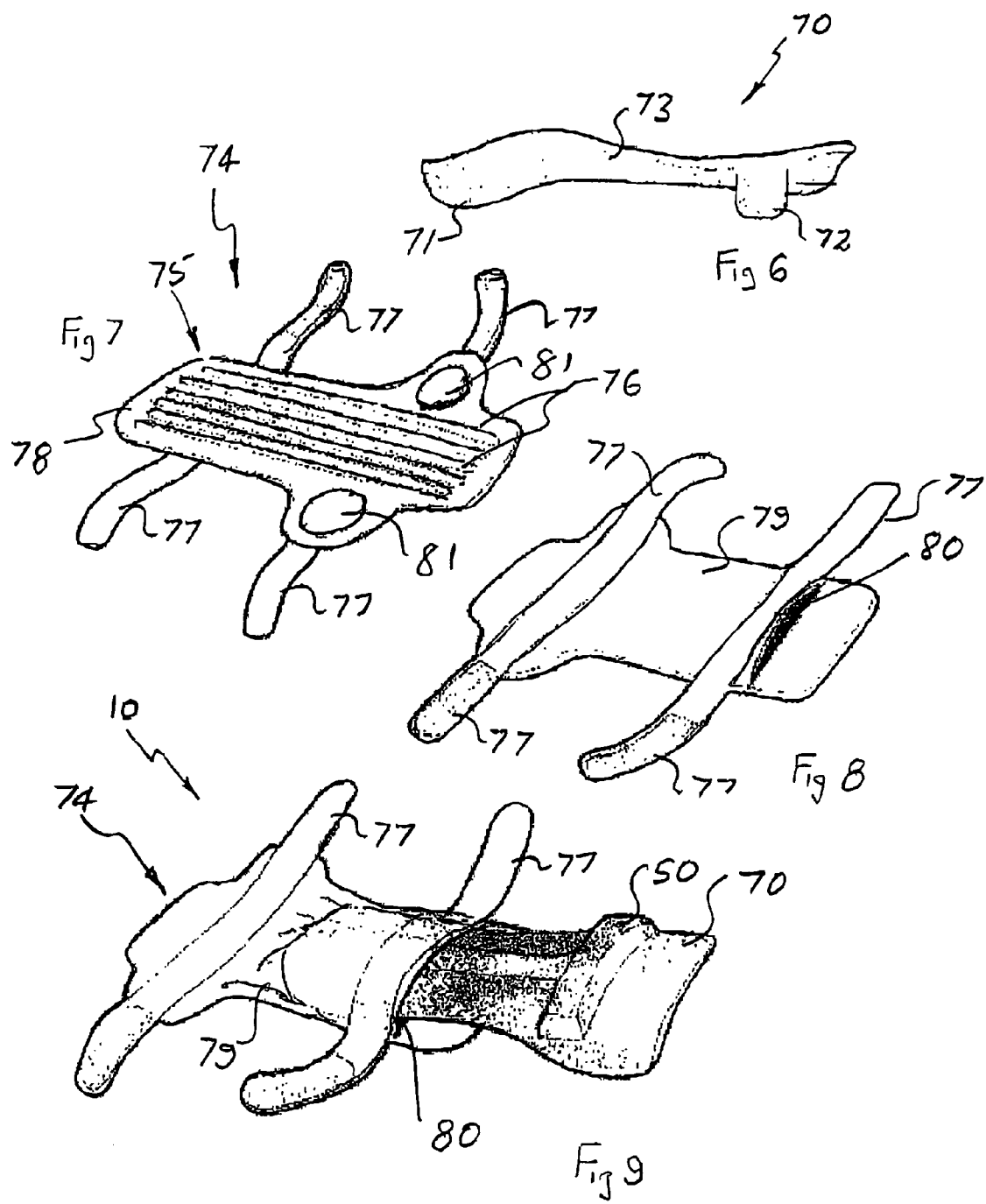

PRESSURE ULCER PROSTHESIS AND METHOD FOR TREATING AND/OR PREVENTING PRESSURE ULCERS

TECHNICAL FIELD

The present invention relates to a prosthesis for treating and/or preventing pressure ulcers. The invention also relates to a method of treating and/or preventing pressure ulcers. More particularly the present invention is directed to a prosthesis and method for treating and/or preventing pressure ulcers on the foot of the patient, and more particularly still, on or around the lateral malleolus and calcaneus of the patient's foot.

BACKGROUND OF THE INVENTION

Immobility, prolonged periods of lying down such as following surgery, peripheral vascular disease and diabetes are all examples of the kinds of things that are associated with pressure sores or pressure ulcers in patients.

Patients who are lying down for prolonged periods are particularly prone to developing pressure ulcers on or around the calcaneus and lateral malleolus of the foot. Patients with diabetes are highly susceptible to developing diabetic foot ulcers caused by poor circulation and patients with peripheral vascular disease are susceptible to developing arterial ulcers.

In such patients, mechanical pressure, moisture, friction and shearing forces all predispose to the development of pressure ulcers (see for example, Harrison's Principles of Internal Medicine, $14^{th}$ edition, Fauci et al (eds), 1998, McGraw Hill, at 43).

There are a wide variety of prosthesis which have been developed for treating and/or preventing pressure ulcers. However, many of these, such as U.S. Pat. No. 4,197,845, U.S. Pat. No. 5,449,339, U.S. Pat. No. 4,186,738 and U.S. Pat. No. 4,104,746 all make some contact with the sole of the patient's foot making it potentially difficult for the patient to walk whilst wearing the prosthesis.

In addition, each of the above mentioned prior art examples, as well U.S. Pat. No. 5,957,874, all have the effect, that when the patient is wearing them and is supine, the height of the patient's foot relative to that of their knee is greater, causing the patient's leg to hyperextend. This can be uncomfortable and is not overcome by the prior art mentioned above.

OBJECT OF THE INVENTION

It is the object of the present invention to overcome or substantially ameliorate at least one of the above disadvantages.

SUMMARY OF THE INVENTION

In a first aspect, the present invention provides a pressure ulcer prosthesis comprising an elongate body to support a patient's limb, said body having:

a longitudinal axis and a longitudinally extending support surface for the limb, said support surface in transverse cross-section being arcuate and concave; and a distal end with a further surface extending from the support surface so as to diverge from the longitudinal axis such that a portion of the limb adjacent the further surface is relieved from pressure.

In one preferred embodiment, the prosthesis body has a transverse cross-section being arcuate and concave. In further embodiments, the prosthesis body is of any other shape, preferably, a shape suitable for accommodating the support surface for the limb and simultaneously providing an appropriate shape capable of enabling a patient wearing the prosthesis to comfortably lie supine on a substantially horizontal surface, such as a bed.

In some preferred embodiments, the prosthesis body has at least one hole for providing ventilation to the area of the limb on which the prosthesis is placed. In alternative embodiments there is a plurality of such holes through the prosthesis body.

In some preferred embodiments, the prosthesis further comprises a liner for lining the support surface and, in further embodiments still, the further surface.

In such embodiments, the liner is formed from a high density foam. In alternative embodiments, the liner is formed from a low density foam, or any other material suitable for improving comfort of a patient wearing the prosthesis.

Further, the liner may have substantially the same shape as the support surface of the prosthesis body or may have a different shape better served to improving the particular patient's comfort. For example a liner surface which remains in contact with the patient's body may have the same contour as that of the patient's body upon which it will be worn.

In other preferred embodiments the prosthesis further comprises at least one reinforcement structure on the outer surface of the prosthesis body for reinforcing the prosthesis' rigidity. In such embodiments, the reinforcement structure is integral with the prosthesis body. In others, the reinforcement structure is connected to or secured by a securing means to the prosthesis body.

In yet still further preferred embodiments, the reinforcement structure extends around a perimeter of the outer surface of the prosthesis body just inwardly from an edge of the perimeter.

In such embodiments, the reinforcement structure has a width and forms a frame-like structure on the outer surface of the prosthesis body In alternative embodiments the reinforcement structure is essentially block-like and covers almost the entire outer surface of the prosthesis body. In further alternative embodiments, the reinforcement structure is a strip running along a longitudinal axis of the outer surface of the prosthesis body. In yet still further alternative embodiments, the reinforcement structure is a strip running along a horizontal axis of the outer surface of the prosthesis body.

In further alternative embodiments there are a plurality of reinforcement structures on the outer surface of the prosthesis body running along either the longitudinal or horizontal axis, or some running along one axis while others running along the opposite axis.

In yet still further alternative embodiments, the reinforcement structures may form a cross-hatched pattern on the outer surface of the prosthesis body, or any other pattern capable of further reinforcing the rigidity of the prosthesis body.

In yet still further preferred embodiments the prosthesis further comprises at least one fitting strap for securing the prosthesis to the patient's limb. The fitting strap can be formed of velcro, or any other material suitable for maintaining the prosthesis in the appropriate position.

In further preferred embodiments there are two fitting straps each located proximal a respective end of the prosthesis. In alternative embodiments there are a plurality of fitting straps on the prosthesis The prosthesis of preferred embodiments further comprises at least one anti-hyperextension means on the outer surface of the prosthesis' body proximal a proximal end of the prosthesis.

The preferred anti-hyperextension means prevents the patient's limb from hyper-extending when the prosthesis is being worn by the patient while the patient is supine on a surface, such as a bed. Hyperextension is caused when the patient's leg comes under a further extension pressure above and beyond that which the patient feels when the patient's leg is naturally fully extended, Preferred anti-hyperextension means have a rectangular prism-type shape but follow a contour of the outer surface of the prosthesis body. Alternative embodiments of the anti-hyperextension means are of any shape provided that the shape allows the anti-hyperextension means to adequately perform its preferred function as described above.

In all such embodiments the anti-hyperextension means may be integral with, connected to, or secured to the prosthesis body. The anti-hyperextension means of the present invention can be formed of any material provided that the material allows the anti-hyperextension means to perform its preferred function as described above.

In a second aspect, the present invention provides a method of treating and/or preventing pressure ulcers on a patient's foot, said method comprising placing a prosthesis of the first aspect on the patient's leg, such that when the patient is supine on a substantially horizontal surface, the prosthesis prevents the calcaneus and lateral malleolus of the patient's foot from contacting the substantially horizontal surface or the prosthesis.

In a third aspect, the present invention provides a prosthesis of the first aspect when used for the treatment and/or prevention of pressure ulcers on a patient's foot.

In preferred embodiments of the method of the second aspect, the prosthesis is placed on the posterior of the patient's lower leg below the popliteal fossa. Preferably, once the prosthesis is so placed, the lower leg is supported such that the patient's foot is suspended when the patient is supine on a substantially horizontal surface. The suspension is such that the patient's lateral malleolus and calcaneus are prevented from coming into contact with the substantially horizontal surface on which the patient is supine, or the prosthesis.

Note that when the patient is supine on a substantially horizontal surface, there is the possibility that because an edge of the distal end of the prosthesis body may elevate the distal end of the patient's leg, the patient's leg will be caused to hyperextend.

As explained earlier, the preferred prosthesis further comprises an anti-hyperextension means. When such prosthesis has been placed on the patient's leg as described above, and the patient is supine on a substantially horizontal surface, the anti-hyperextension means preferably rests on the substantially horizontal surface. As a consequence, the anti-hyperextension means preferably ensures that the patient's knee is at the same relative height as his/her foot, or is relatively higher than his/her foot, with respect to the substantially horizontal surface. In that way the anti-hyperextension means preferably prevents the patient's leg from hyperextending.

Also as explained earlier, a preferred prosthesis further comprises at least one fitting strap for securing the prosthesis to the patient's leg. There are at least two advantages associated with securing the prosthesis to the patient's leg. First, the prosthesis is unlikely to be dislodged from its appropriate position if the patient moves. Second, the patient is free to ambulate without having to remove the prosthesis. Indeed, when the prosthesis is placed on the patient's leg as discussed above, no part of the prosthesis would interfere with the patient's ability to walk whilst wearing it.

BRIEF DESCRIPTION OF THE DRAWINGS

A preferred form of the present invention will now be described by way of example with reference to the accompanying drawings wherein:

FIG. 6 is a schematic side elevation of a moulded insert employed in a modification of the prosthesis of FIG. 1.

FIG. 7 is a schematic top isometric view of a sleeve to cover the insert of FIG. 6.

FIG. 8 is a schematic bottom isometric view of the sleeve of FIG. 7.

FIG. 9 is a schematic isometric view of the insert of FIG. 6 being inserted in the sleeve of FIGS. 7 and 8.

DETAILED DESCRIPTION OF THE PREFERRED EMBODIMENTS

Figure 1:
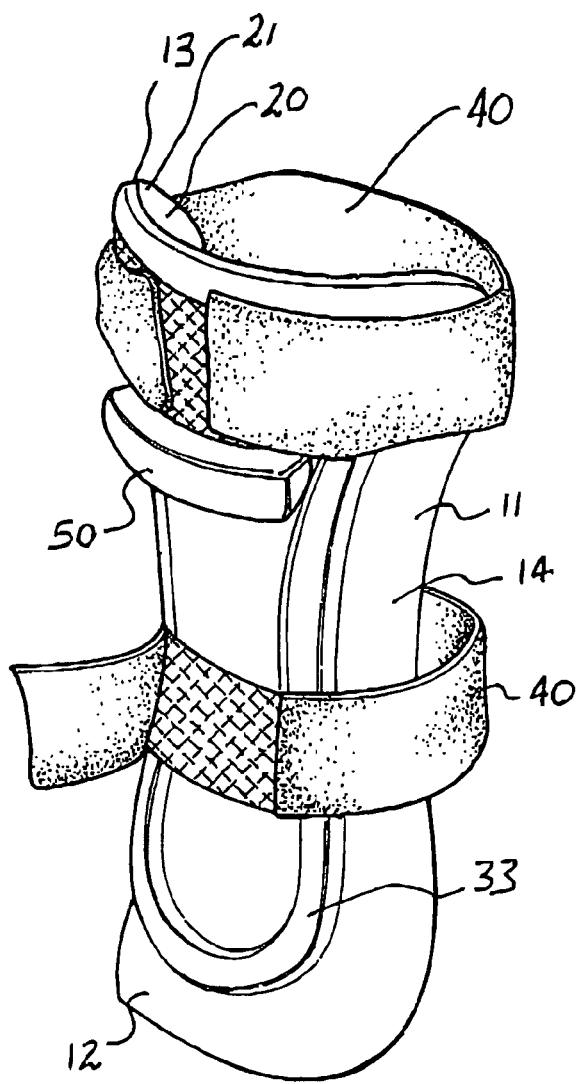
FIG. 1 is a rear perspective view of a preferred embodiment of the pressure ulcer prosthesis of the present invention.
Figure 2:
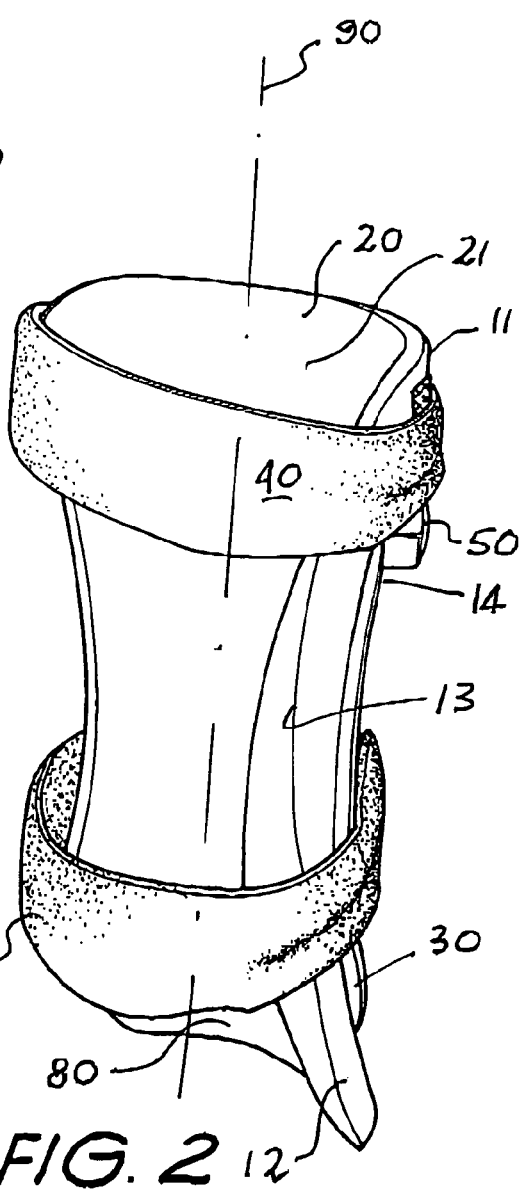
FIG. 2 is a front perspective view of a preferred embodiment of the pressure ulcer prosthesis of the present invention.

The pressure ulcer prosthesis 10 of the preferred embodiment of the present invention comprises an elongate body 11 to support a patient's limb, said body 11 having: a longitudinal axis 90 and a longitudinally extending support surface 13 for the limb, said support surface 13 in transverse cross-section being arcuate and concave; and a distal end 12 with a further surface 80 extending from the support surface 13 so as to diverge from the longitudinal axis 90 such that a portion of the limb adjacent the further surface 80 is relieved from pressure.

In preferred embodiments, the body 11 in transverse cross-section is arcuate and concave.

The preferred prosthesis 10 further comprises a liner 20 for lining the support surface 13 of the prosthesis body 11. The liner 20 is preferably formed from a high density foam. Preferably, the liner 20 has substantially the same shape as the support surface 13 of the prosthesis body 11. Of course, where appropriate, a liner surface 21 which remains in contact with the patient's body may have the same contour of the patient's body on which it will be worn.

The preferred prosthesis 10 further comprises at least one reinforcement structure 30 on an outer surface 14 of the prosthesis body 11 for reinforcing the prosthesis's rigidity.

As shown in FIG. 1, the reinforcement structure 30 of preferred embodiments extends around a perimeter of the outer surface 14 of the prosthesis body 11 just inwardly from an edge of the perimeter.

In such embodiments, the reinforcement structure 30 has a width and forms a frame-like structure on the outer surface 14 of the prosthesis body 11.

As is illustrated in FIGS. 1–3 and 5, the preferred prosthesis 10 further comprises two fitting straps 40 for securing the prosthesis 10 to the patient's body. The preferred fitting straps 40 are formed of velcro. Typically, the fitting straps 40 are each located proximal a respective end of the prosthesis 10.

The prosthesis 10 of preferred embodiments further comprises at least one anti-hyperextension means 50 on the outer surface 14 of the prosthesis body 11 proximal a proximal end of the prosthesis 10.

As shown in FIG. 1, preferred anti-hyperextension means 50 has a rectangular prism-type shape but follows a contour of the outer surface 14 of the prosthesis body 11.

As discussed above, the preferred anti-hyperextension means 50 preferably prevents the patient's limb from hyperextending when the prosthesis 10 is being worn by the patient while the patient is supine on a substantially horizontal surface 70, such as a bed. This particular function of the anti-hyperextension means 50 is discussed in more detail below.

Preferred embodiments of the present invention also provide a method of treating and/or preventing pressure ulcers on a patient's foot 60. The preferred method comprises placing a prosthesis 10 on the posterior 63 of the patient's lower leg 68 below the popliteal fossa 64.

Figure 3:
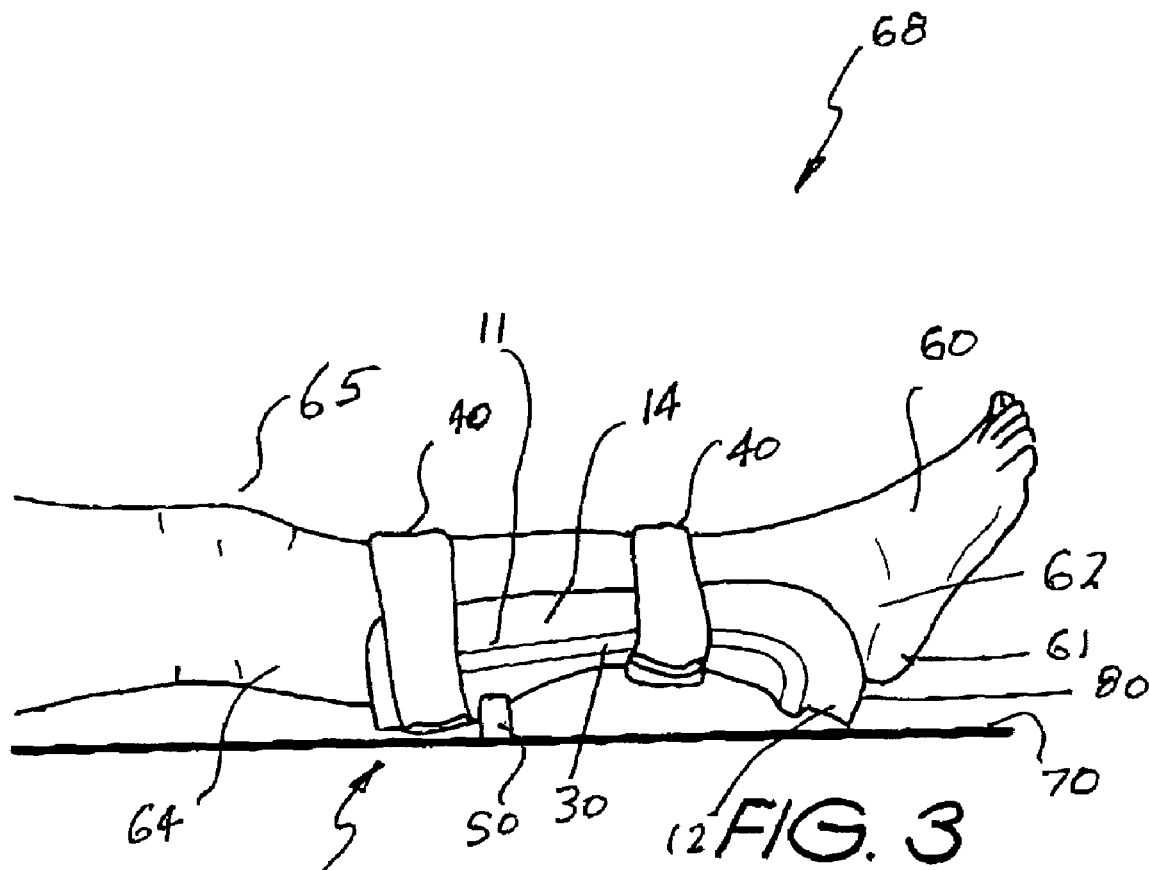
FIG. 3 is a schematic diagram illustrating a preferred embodiment of the pressure ulcer prosthesis of the present invention being worn by a patient in the appropriate position.
Figure 4:
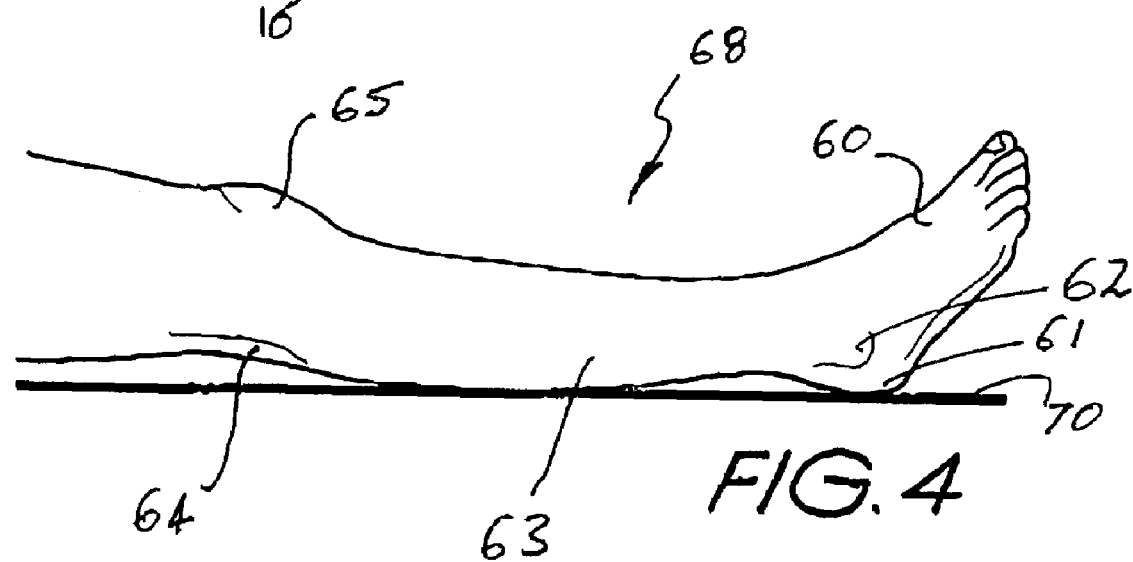
FIG. 4 is a schematic diagram of the lower leg of the patient.
Figure 5:
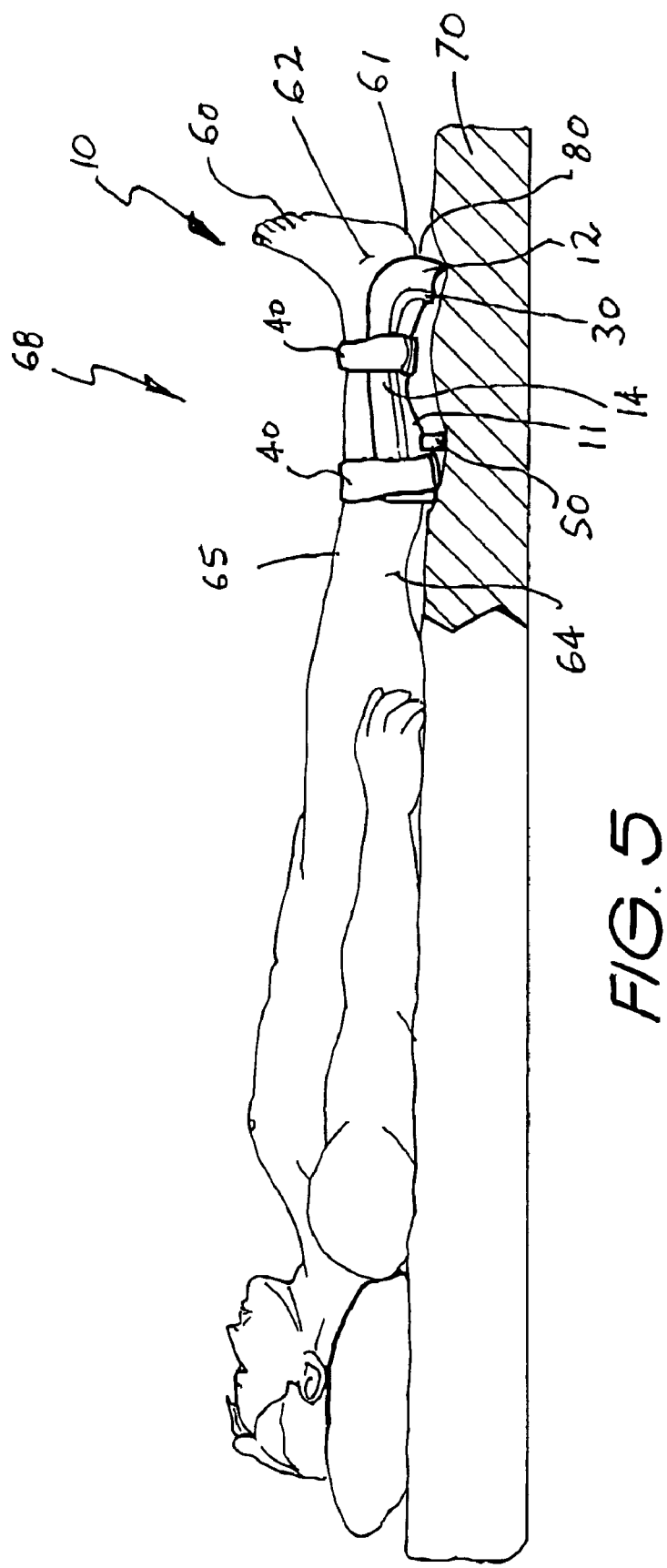
FIG. 5 is a schematic diagram illustrating a patient lying on a bed wearing a pressure ulcer prosthesis of the present invention.

Once the prosthesis 10 is so placed, the lower leg 68 is preferably supported such that the patient's foot 60 is suspended when the patient is supine on a substantially horizontal surface 70, as shown in FIGS. 3 and 5. The suspension is such that the patient's lateral malleolus 62 and calcaneus 61 are prevented from coming into contact with the substantially horizontal surface 70 on which the patient is supine, or the prosthesis 10.

As can be seen in FIGS. 3 and 5, when the patient is supine on a substantially horizontal surface 70, there is the possibility that because an edge of the distal end 12 of the prosthesis body 11 effectively elevates the distal end of the patient's lower leg 68, the patient's leg will be caused to hyperextend. As discussed earlier, hyperextension is caused when the patient's leg comes under a further extension pressure above and beyond that which the patient feels when the patient's leg is naturally fully extended.

Accordingly, preferred embodiments of the invention disclose that when the prosthesis 10 is properly placed on the patient's lower leg 68, the anti-hyperextension means 50 rests on the substantially horizontal surface 70 in such a way as to ensure that the patient's knee 65 is at the same relative height as the patient's foot 60, or is relatively higher than the patient's foot 60, with respect to the substantially horizontal surface 70. In that way, the anti-hyperextension means 50 preferably prevents the patient's leg from hyperextending.

As explained earlier, the fitting straps 40 secure the prosthesis 10 to the patient's leg. Having such straps provides the advantage that the prosthesis 10 is unlikely to be dislodged from its appropriate position if the patient moves around whilst lying on a substantially horizontal surface 70, such as a bed. The further advantage is that when the prosthesis is placed on the patient's leg as discussed above, no part of the prosthesis 10 would interfere with the patient's ability to walk whilst wearing it.

In the embodiment of FIG. 6 to 9 the prosthesis 10 includes a moulded insert 70 formed of plastics or rubber (natural or synthetic). Typically the insert 70 would be moulded is a series of sizes to accomodate different patients. The insert 70 supports a patient's limb and has a support surface that is acurate and concave as described with reference to the previous embodiment. The insert 70 also is provided with a distal end 71 and an anti-hyperexstention means 72 in the front of a block extending downwardly from the longitudinal body 73 of the insert 70, again as described with reference to the previous embodiment.

The insert 70 is removeably inserted in a sleeve 74 that has an upper surface 75 provided with a plurality of longitudinally extending ribs 76. The sleeve 74 further includes straps 77 that pass about the patient's leg to secure the prosthesis 10 to the patient's leg. The sleeve 74 includes an upper sheet 78 provided with the ribs 76, and a lower sheet 79 secured to the upper sheet 78 and cooperating therefore to provide a pocket 80 within which the insert 70 is located. The sheets 78 and 79 are preferably fabric.

Use of the above described sleeve 74 has hygiene advantages in that the sleeve 75 is easily replaced. A further advantage is ease of laundering. Preferably the sheet 78 is of a texture so that it is comfortable in respect of contact with the skin and provides ventilation. Preferably the sheet 78 also has ankle protector pads 81 that provide a cushioned area for contact with the patient's ankle. In an alternative arrangement the pads 81 are replaced with cavities into which the ankle prosthesis extend.

Preferably the insert 70 and sleeve 74 are symmetrical about a central longitudinal planes that the prosthesis can be worn on the left and right legs.

The claims defining the invention are as follows:

1. A pressure ulcer prosthesis comprising an elongate body to support a patient's limb, said body having:
   a longitudinal axis and a longitudinally extending support surface adapted to receive an underside of a limb, said support surface in transverse cross-section being arcuate and concave;
   at least one anti-hyperextension means on an outer surface of the prosthesis body proximal a proximal end of the prosthesis, wherein the anti-hyperextension means has a rectangular prismatic shape and follows a contour of the outer surface of the body; and
   a distal end with a further surface extending from the support surface so as to diverge from the longitudinal axis such that a portion of the limb adjacent the further surface is relieved from pressure.

2. The prosthesis of claim 1, wherein, the prosthesis body has a lower surface that in transverse cross-section is arcuate and concave.

3. The prosthesis of claim 1, wherein, the prosthesis body is a shape suitable for accommodating the support surface for the limb and simultaneously providing an appropriate shape capable of enabling a patient wearing the prosthesis to comfortably lie supine on a substantially horizontal surface.

4. The prosthesis of claim 1, wherein, the prosthesis body has at least one hole for providing ventilation to an area of the limb on which the prosthesis is placed.

5. The prosthesis of claim 4, wherein there is a plurality of holes through the prosthesis body.

6. The prosthesis of claim 1, wherein, the prosthesis further comprises a liner for lining the support surface.

7. The prosthesis of claim 6, wherein the liner is formed from a high density foam.

8. The prosthesis of claim 6, wherein the liner is formed from a low density foam.

9. The prosthesis of claims 6, wherein, the liner is substantially the same shape as the support surface of the prosthesis body.

10. The prosthesis of claim 1, wherein the prosthesis further comprises at least one reinforcement structure on an outer surface of the prosthesis body for reinforcing the prosthesis' rigidity.

11. The prosthesis of claim 10, wherein the reinforcement structure is integral with the prosthesis body.

12. The prosthesis of claim 10 wherein the reinforcement structure extends around a perimeter of the outer surface of the prosthesis body just inwardly from an edge of the perimeter.

13. The prosthesis of claim 12, wherein the reinforcement structure has a width and forms a frame-like structure on an outer surface of the prosthesis body.

14. The prosthesis of claim 10, wherein the reinforcement structure is essentially block-like and covers almost the entire outer surface of the prosthesis body.

15. The prosthesis of claim 10, wherein the reinforcement structure is a strip running along a longitudinal axis of the outer surface of the prosthesis body.

16. The prosthesis of claim 10, wherein, the reinforcement structure is a strip running along a horizontal axis of the outer surface of the prosthesis body.

17. The prosthesis of claim 1, further including a plurality of reinforcement structures on the outer surface of the prosthesis body running along either longitudinally or transverse of the prosthesis.

18. The prosthesis of claim 10, wherein the reinforcement structures form a cross-hatched pattern on the outer surface of the prosthesis body, or any other pattern capable of further reinforcing the rigidity of the prosthesis body.

19. The prosthesis of claim 1, further comprises at least one fitting strap for securing the prosthesis to the patient's limb.

20. The prosthesis of claim 19, wherein there are two fitting straps each located proximal a respective end of the prosthesis.

21. A method for treating or preventing pressure ulcers in a lower leg of a patient, comprising
   (a) providing the pressure ulcer prosthesis of claim 1, and
   (b) securing the elongate body to the underside of the lower leg below the popliteal fossa such that, when the patient is supine on a substantially horizontal surface, the foot of the lower leg is suspended with a lateral malleolus and calcaneus of the foot prevented from coming into contact with the substantially horizontal surface or the elongate body.

22. A prosthesis for treating or preventing pressure ulcers in a lower leg of a patient, the prosthesis comprising:
   (a) body means, comprising an elongate body, for supporting the lower leg such that, when the patient is supine on a substantially horizontal surface, a foot of the lower leg is suspended with a lateral malleolus and calcaneus of the foot prevented from coming into contact with the substantially horizontal surface or the body means, the elongate body having a longitudinal axis and a longitudinally extending support surface, said support surface in traverse cross-section being arcuate and concave, said elongate body having a distal end with a further surface extending from the support surface so as to diverge from the longitudinal axis, said elongate body comprising anti-hyperextension means for ensuring that, when the patient is supine on the substantially horizontal surface, the foot is suspended above the substantially horizontal surface at a height that is the same as or lower than a height at which a knee of the lower leg is disposed above the substantially horizontal surface, the anti-hyperextension means being disposed on an outer surface of the elongate body proximal a proximal end of the prosthesis; and
   (b) means for securing the elongate body to the lower leg.

23. The prosthesis of claim 1, including a sleeve within which said body is located.

24. The prosthesis of claim 23, wherein said sleeve includes a pair of sheet members secured together and enclosing a pocket within which the body is located.

25. The prosthesis of claim 23, wherein said sleeve is provided with padded areas to engage a patient's ankles.

26. The prosthesis of claim 23, wherein said sleeve has a cavity to receive an insert.

27. The prosthesis of claim 1 wherein the prosthesis is symmetrical about a central longitudinal plane, and is adapted to be worn on either a left or right limb.

28. The prosthesis of claim 10, wherein the reinforcement structure is connected, or secured by securing means, to the prosthesis body.

29. The prosthesis of claim 22, wherein, the anti-hyperextension means have a rectangular prismatic shape and follows a contour of the outer surface of the elongate body.

* * * * *

UNITED STATES PATENT AND TRADEMARK OFFICE
CERTIFICATE OF CORRECTION

| | | |
|---|---|---|
| PATENT NO. | : 7,222,625 B2 | |
| APPLICATION NO. | : 11/031675 | |
| DATED | : May 29, 2007 | |
| INVENTOR(S) | : David E. Huber | |

It is certified that error appears in the above-identified patent and that said Letters Patent is hereby corrected as shown below:

Delete Drawing Sheet 4 of 4 consisting of figures 6-9 and insert Drawing Sheet 4 of 4 with figures 6-9 as shown on the attached page.

Col. 6, line 16 "prosthesis 10" should be changed to --insert 70--.

Col. 6, line 22, "sleeve 75" should be changed to --sleeve 74--.

Signed and Sealed this
Fifth Day of June, 2012

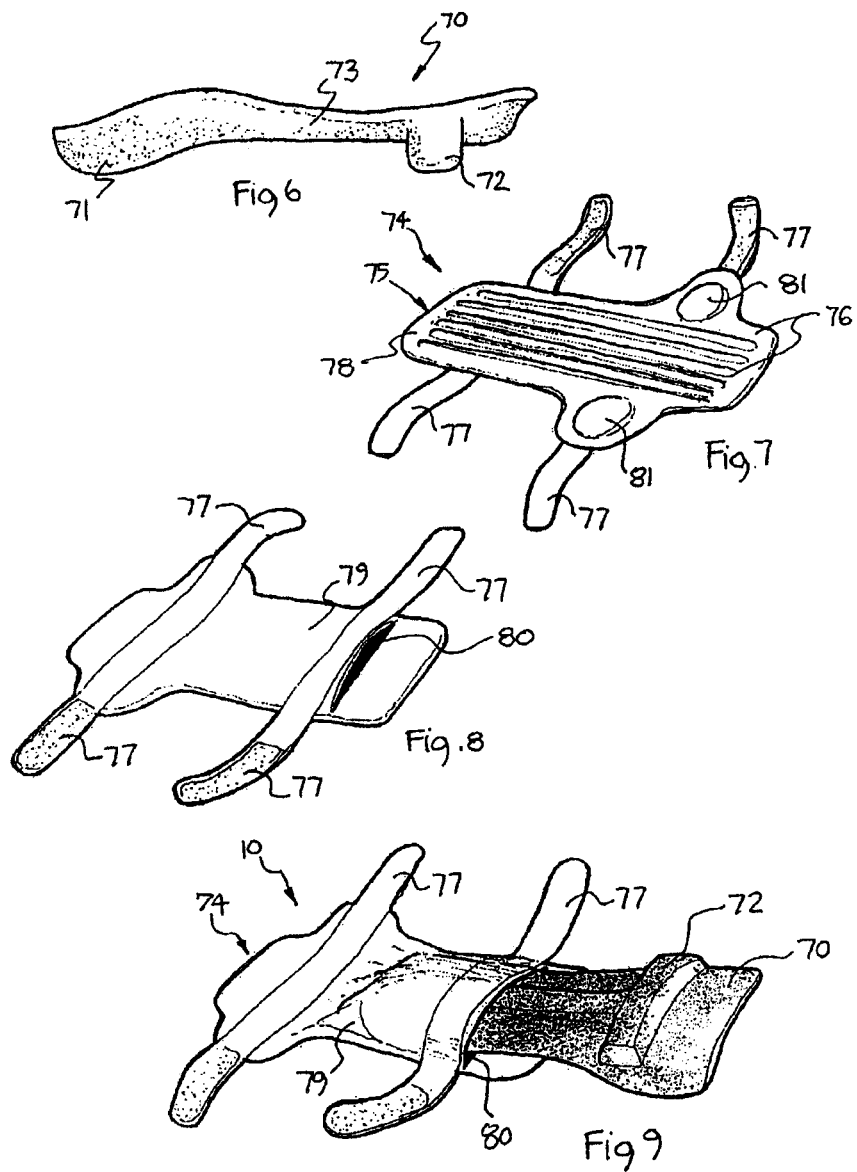

David J. Kappos
*Director of the United States Patent and Trademark Office*